(12) United States Patent
Castellin et al.

(10) Patent No.: US 8,609,841 B2
(45) Date of Patent: Dec. 17, 2013

(54) METHOD FOR THE PREPARATION OF ERLOTINIB

(75) Inventors: Andrea Castellin, Padova (IT); Ottorino De Lucchi, Venice (IT); Andrea Caporale, Venice (IT)

(73) Assignee: F.I.S. Fabbrica Italiana Sintetici S.p.A., Alte di Montecchio Maggiore (IT)

( * ) Notice: Subject to any disclaimer, the term of this patent is extended or adjusted under 35 U.S.C. 154(b) by 0 days.

(21) Appl. No.: 13/272,888

(22) Filed: Oct. 13, 2011

(65) Prior Publication Data

US 2012/0095228 A1    Apr. 19, 2012

(30) Foreign Application Priority Data

Oct. 14, 2010   (IT) .............................. MI2010A1878
Mar. 24, 2011   (IT) .............................. MI2011A0464

(51) Int. Cl.
    *C07D 239/94*   (2006.01)
(52) U.S. Cl.
    USPC ........................................................ 544/293
(58) Field of Classification Search
    USPC ........................................................ 544/293
    See application file for complete search history.

(56) References Cited

U.S. PATENT DOCUMENTS

| | | | |
|---|---|---|---|
| 4,219,679 A | 8/1980 | Onopchenko et al. | |
| 5,902,902 A | 5/1999 | Cabri et al. | |
| 6,476,040 B1 * | 11/2002 | Norris et al. | 514/266.4 |
| 2006/0188498 A1 | 8/2006 | Ashkenazi | |
| 2006/0224016 A1 * | 10/2006 | Urazoe et al. | 564/305 |

FOREIGN PATENT DOCUMENTS

| | | |
|---|---|---|
| EP | 1 044 969 A2 | 10/2000 |
| WO | WO 96/30347 A1 | 10/1996 |
| WO | WO 01/34574 A1 | 5/2001 |
| WO | WO2009/009778 * | 1/2009 |

OTHER PUBLICATIONS

Zhang et al, 2010, J. Org. Chem, vol. 75, p. 5259-5264.*
Zhao, 2010, Chem. Comm, vol. 46, p. 9049-9051.*
Baby, 2000, Applied Catalysis A: General 195-195, p. 203-211.*

* cited by examiner

*Primary Examiner* — Yong Chu
*Assistant Examiner* — Karen Cheng
(74) *Attorney, Agent, or Firm* — Dickstein Shapiro LLP

(57) ABSTRACT

An alternative method for the preparation of Erlotinib through a new chemical reaction for the preparation of the 4-(3-aminophenyl)-2-methyl-3-butyn-2-ol key intermediate of formula (IV) according to the following scheme.

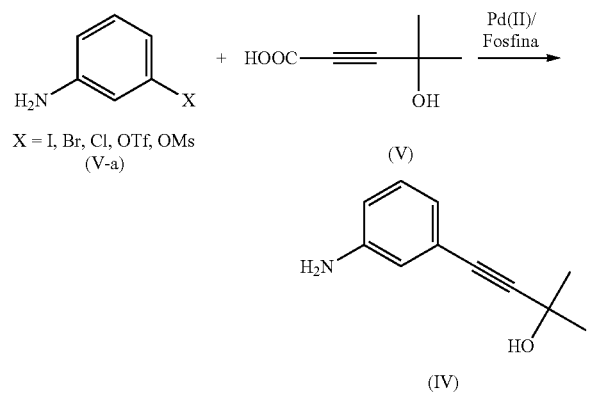

16 Claims, No Drawings

METHOD FOR THE PREPARATION OF ERLOTINIB

This application claims priority under 35 U.S.C. §119 to Italian Application Nos. MI2010A001878, filed Oct. 14, 2010 and MI2011A000464, filed Mar. 24, 2011.

TECHNICAL FIELD OF THE INVENTION

A method for the preparation of the pharmaceutical active ingredient called Erlotinib forms an object of the present invention.

STATE OF THE ART

Erlotinib hydrochloride is the pharmaceutical active ingredient on which TARCEVA, a drug that is very efficient and widely used for the treatment of lung cancer, is based on. Actually, Erlotinib hydrochloride acts as an EGFR TK inhibitor.

Erlotinib hydrochloride, of formula (I) and CAS Registry Number 183319-69-9, is a quinazoline-derivative having the chemical name of N-(3-ethynylphenyl)-6,7-bis(2-methoxyethoxy)-4-quinazoline hydrochloride, molecular formula $C_{22}H_{23}N_3O_4 \cdot HCl$, molecular weight 429.89 and pKa of 5.42 at 25° C.

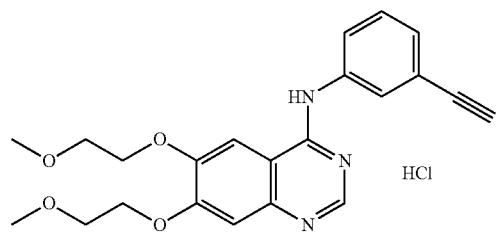

(I)

The Erlotinib hydrochloride used for the preparation of the medicinal specialty is a yellowish-white anhydrous crystalline solid, non-hygroscopic, having crystalline form A which is the most thermodynamically stable among the various known polymorph forms A, B, E and L.

The first known method for the preparation of Erlotinib is described in the example 20 of the published international application WO 96/30347 and described according to the following scheme:

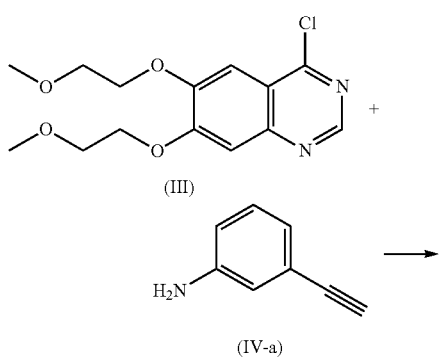

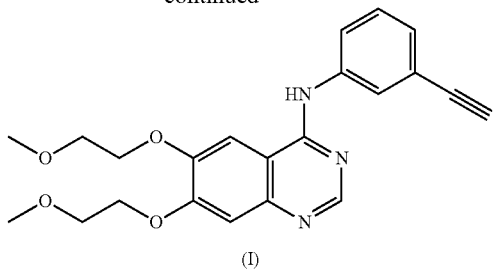

(I)

in which 3-ethynylanyline of formula (IV-a) is reacted with 4-chloro-6,7-bis(2-methoxyethoxy)quinazoline of formula (III) in isopropanol in presence of pyridine to provide Erlotinib of formula (I) which, after purification in a chromatographic column, is obtained in a subsequent step in salified form with 71% molar yield. In order to avoid the chromatrographic purification, a method based on a cleaner coupling reaction was described in EP 1 044 969 B1 in examples 1, 2 and 3. Example 1 is schematised below:

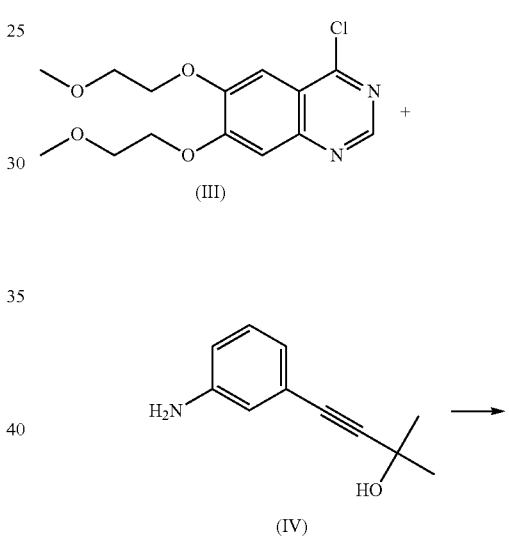

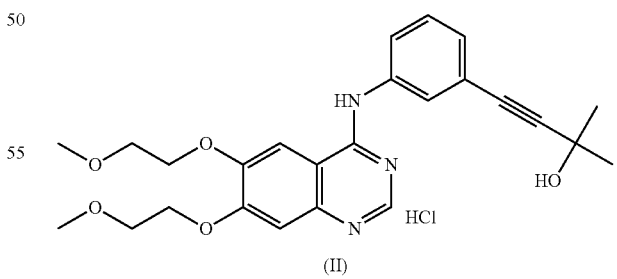

in which 4-(3-aminophenyl)-2-methyl-3-butyn-2-ol of formula (IV) is reacted with 4-chloro-6,7-bis(2-methoxyethoxy)quinazoline of formula (III) in acetonitrile at reflux to provide 3-butyn-2-ol intermediate, 4-[3-[[6,7-bis(2-methoxyethoxy)-4-quinazolinyl]amine]phenyl]-2-methyl, hydrochloride (1:1) of formula (II) with 100% molar yield.

In example 2, schematized below,

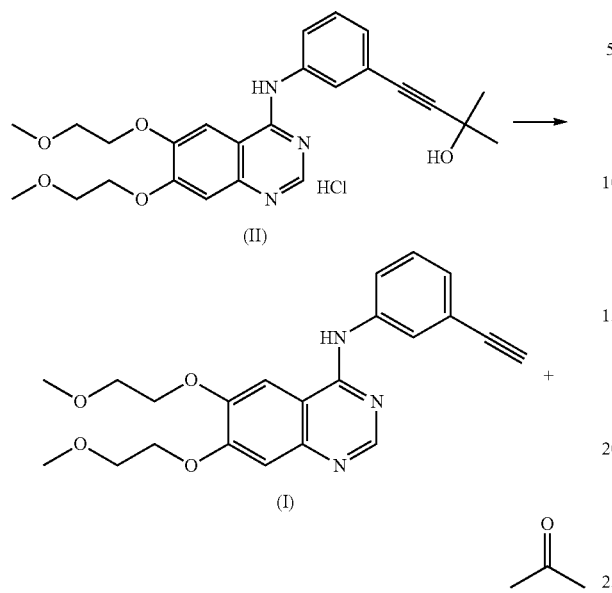

3-Butyn-2-ol, 4-[3-[[6,7-bis(2-methoxyethoxy)-4-quinazolinyl]amine]phenyl]-2-methyl, hydrochloride (1:1) of formula (II) is treated with sodium hydroxide in water and acetate ethyl, removing the protection of the acetylenic function releasing acetone and providing Erlotinib of formula (I) with 86% molar yield. Example 3 describes the obtainment of Erlotinib hydrochloride and purification through crystallisation from 1-butanol.

With respect to the first described method, this synthetic method has the advantage lying in the fact that the protection of the acetylenic function leads to coupling reactions with the intermediate of formula (III) with lesser by-products.

Thus, the 4-(3-aminophenyl)-2-methyl-3-butyn-2-ol intermediate of formula (IV) plays a key role in the synthesis of the Erlotinib.

The main methods known today for the preparation of the 4-(3-aminophenyl)-2-methyl-3-butyn-2-ol intermediate of formula (IV) are described by Bleicher Leo et al. in Synlett (1995), (11), 1115-1116 and by Walter Cabri et al. In U.S. Pat. No. 5,902,902. Both mentioned references provide for the synthesis of the intermediate of formula (IV) through the following scheme:

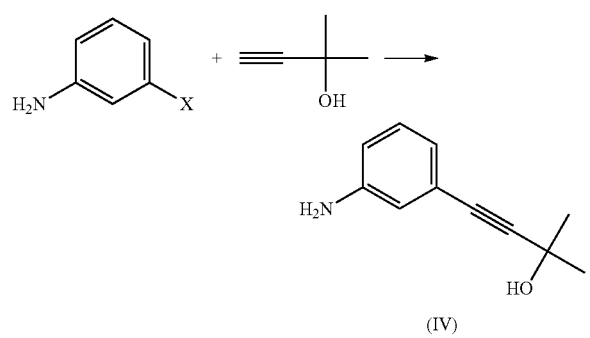

in which aloanyline is reacted with 2-methyl-3-butynol, a monosubstituted acetylene, in presence of a catalytic system based on Palladium/triphenylphosphine and cupreous iodide or chloride. In U.S. Pat. No. 5,902,902 the catalytic system is based on Pd(II) while Pd(0) on carbon is used in the reference literature, but both provide for the essential presence of copper.

Thus, the main drawback represented by these procedures lies in the presence—in the wastes—of copper, which, being a toxic metal, makes disposal thereof complex.

Lastly, in Example 4 of the published International application WO 01/34574 A1 there is described the conversion schematized below:

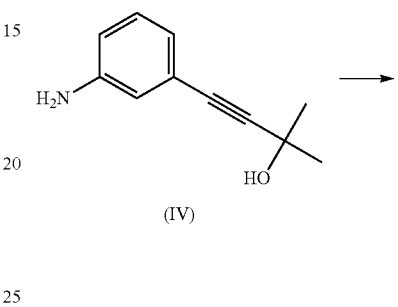

in which 4-(3-aminophenyl)-2-methyl-3-butyn-2-ol of formula (IV) is converted into 3-ethynylanyline of formula (IV-a) through treatment with sodium hydroxide in toluene.

This conversion allows considering the 4-(3-aminophenyl)-2-methyl-3-butyn-2-ol intermediate of formula (IV) interesting for the synthesis of Erlotinib even applying the method for synthesis described in WO 96/30347.

SUMMARY OF THE INVENTION

The problem addressed by the present invention is thus providing an alternative method for the preparation of the Erlotinib, through the 4-(3-aminophenyl)-2-methyl-3-butyn-2-ol intermediate of formula (IV), overcoming the need of using toxic metals in the synthesis with reference to the known art.

Such problem is solved by a method for the synthesis of Erlotinib as outlined in the attached claims, whose definitions form an integral part of the present description.

Further characteristics and advantages of the process according to the invention will be clear from the following description of preferred embodiments, provided by way of non-limiting example.

DETAILED DESCRIPTION OF THE INVENTION

The present invention regards a method for the preparation of Erlotinib of formula (I) or a salt thereof:

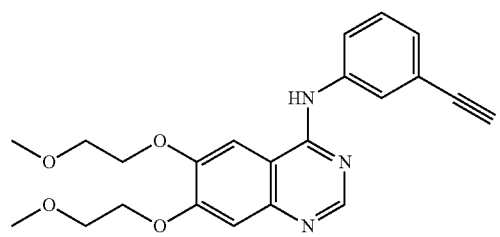

(I)

through the method below, comprising the following steps:

(a) Reaction of the 3-substituted aniline of formula (V-a) where X is selected from the group consisting in I, Br, Cl, OTs, OMs with 4-hydroxy-4-methyl-2-pentinoic acid of formula (V) according to the following scheme:

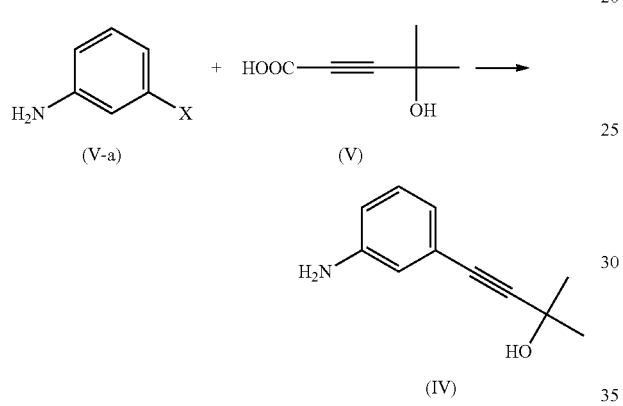

to obtain 4-(3-aminophenyl)-2-methyl-3-butyn-2-ol of formula (IV);

(b) Reaction of the intermediate of formula (IV) with 4-chloro-6,7-bis(2-methoxyethoxy)quinazoline of formula (III) to obtain 3-Butyn-2-ol, 4-[3-[[6,7-bis(2-methoxyethoxy)-4-quinazolinyl]amine]phenyl]-2-methyl, hydrochloride (1:1) of formula (II) according to the following scheme:

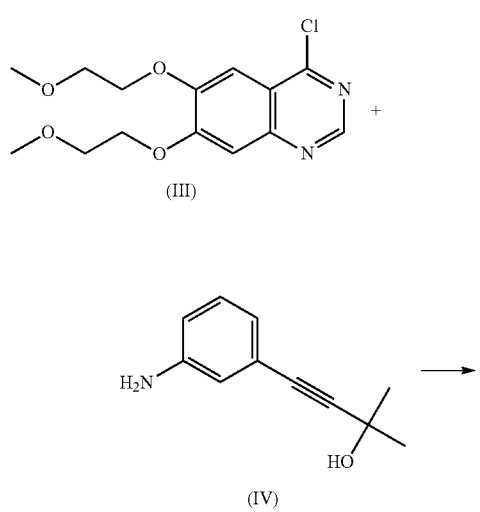

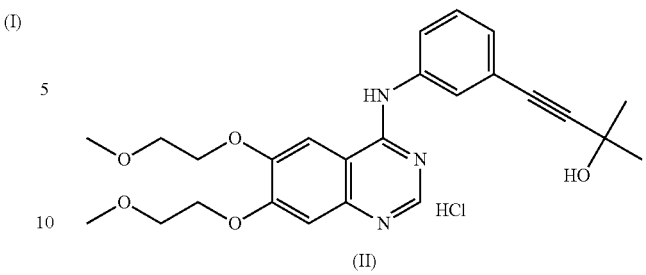

(II)

(c) Conversion of the intermediate (II) to Erlotinib of formula (I) according to the following scheme.

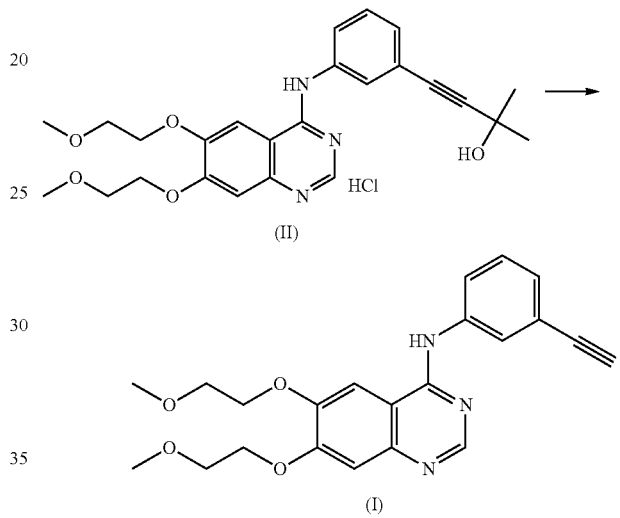

The Erlotinib thus obtained can be conveniently converted into Erlotinib hydrochloride through the prior art methods.

It was surprisingly discovered that the reaction of the 3-substituted aniline with a disubstituted derivative of acetylene such as 4-hydroxy-4-methyl-2-pentinoic acid of formula (V), may occur due to the presence of a catalytic system constituted by Palladium (II)/Phosphine ligand.

Such new reaction does not require the use of Copper in the catalytic system and provides for the simultaneous decarboxylation upon the introduction of alkynyl in the aromatic cycle.

The balanced reaction is indicated below:

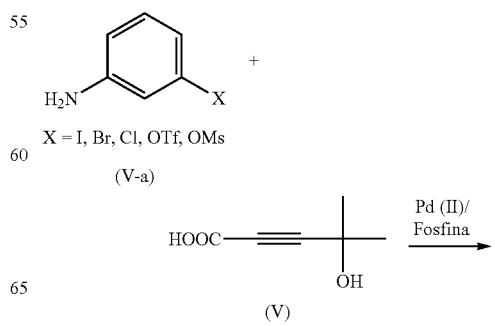

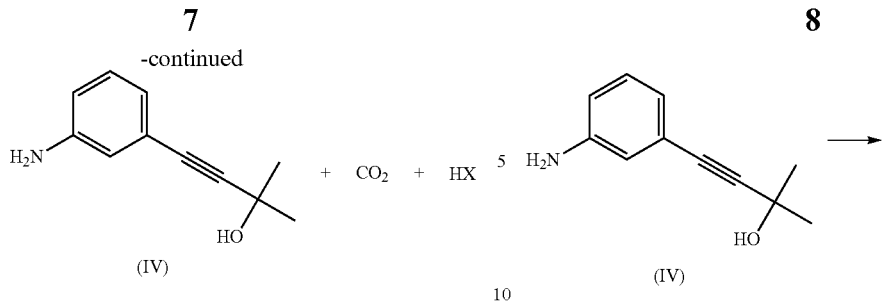

The initial 3-substituted aniline has a substituent in position 3 selected in the group consisting of Iodine, Bromine, Chlorine, O-Tf (triflyl(trifluoromethanesulfonyl)) and O-Ms (mesylate).

Such reaction is catalysed by a catalytic system comprising Palladium(II) in form of salt and a phosphine ligand.

Palladium can be conveniently used as Pd(II) acetate or as trifluoroacetate. The amount of palladium used may vary between 1 and 10% molar with respect to the 3-substituted aniline. Better results are attained when palladium is at least 5% molar, while the conversion is lower when amounts lower than 5% molar are used. The phosphine ligand may be conveniently selected from among XPhos (2-Dicyclohexylphosphino-2',4',6'-triisopropylbiphenyl, RN 564483-18-7), SPhos (2-Dicyclohexylphosphino-2',6'-dimethoxybiphenyl, RN 657408-07-6) and generally among the phosphine ligands of biphenyl type most of which are widely available in the market.

Preferably, the ligand used is SPhos.

The reaction is facilitated by the presence of tetra-n-butylammonium fluoride (TBAF) at amounts up to 5 equivalent, preferably about 3.0 molar equivalents with respect to the 3-substituted aniline. The reaction can be conducted in a solvent, preferably of the ether type, more preferably in THF.

The reaction can be conducted between 60° and 100° C., preferably at about 80° C.

The reaction provides optimal results when the initial 3-substituted aniline is 3-Bromoaniline.

The 4-hydroxy-4-methyl-2-pentinoic acid of formula (V), having RN 50624-25-4, is a substance available in the market for example from ChemBridge Corporation (San Diego, Calif., 92127 USA) or Matrix Scientific (Columbia, S.C., 29224 USA) or it can be conveniently prepared through the following reaction:

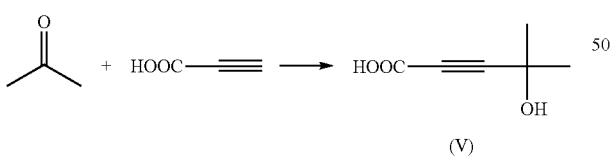

in which acetone is reacted with the propargylic acid (i.e. 2-propionic acid).

Such reaction is conducted in presence of a strong base such as potassium hydroxide. Various solvents such as THF, toluene and acetone or mixtures thereof can be used. Acetone is the preferred solvent. The product can be isolated in crystalline form from dichloromethane. According to a variant of the method of the invention, the steps (b) and (c) can be replaced by the following steps:

(d) conversion of the intermediate (IV) to 3-ethynylanyline of formula (IV-a) according to the following reaction:

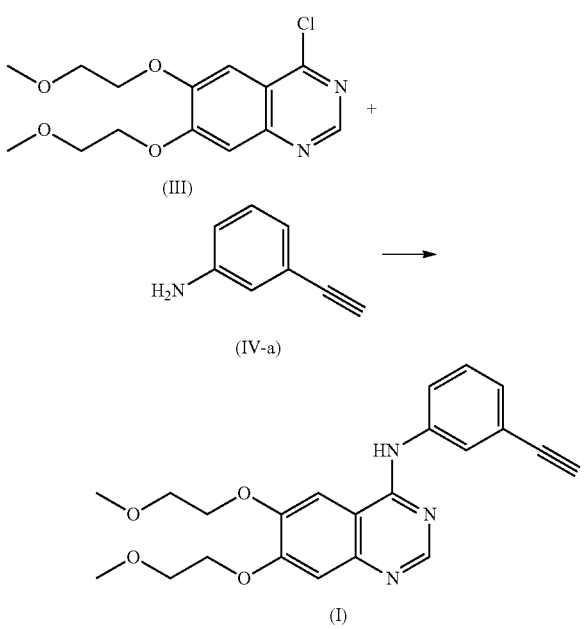

(e) Reaction of the intermediate of formula (IV-a) with 4-chloro-6,7-bis(2-methoxyethoxy)quinazoline of formula (III) to obtain Erlotinib of formula (I) according to the following scheme:

A further variant of the method according to present invention provides for starting from a compound having a substituent that can be easily transformed into an amino group. Such method comprises the following steps:

(f) Reaction of the compound of formula (V-b)

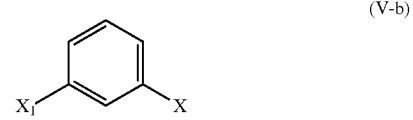

where X is selected from the group consisting in Iodine, Bromine, Chlorine, OTs, OMs; and X1 is selected in the group consisting in nitro, NH(C=O)R in which R is a C1-C4 alkyl or it is OR2 in which R2 is a C1-C4 alkyl or benzyl; with the 4-hydroxy-4-methyl-2-pentinoic acid of formula (V):

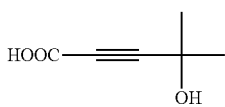

to obtain the compound of formula (IV-b):

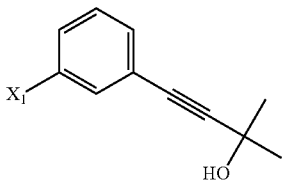

in which X1 has the same meaning as above;
(g) Conversion of the intermediate of formula (IV-b) to 4-(3-aminophenyl)-2-methyl-3-butyn-2-ol of formula (IV):

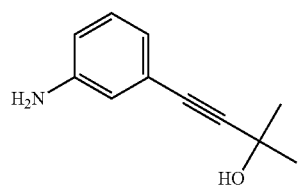

(h) Conversion of 4-(3-aminophenyl)-2-methyl-3-butyn-2-ol of formula (IV) to Erlotinib according to steps (b) and (c).
A further variant of the latter method is constituted by a method in which said steps (g) and (h) are replaced by the following steps:
(i) conversion of the intermediate (IV-b) to compound of formula (IV-b-a):

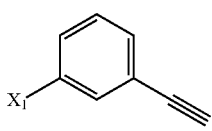

in which X1 has the same meaning as above;
(j) conversion of the intermediate (IV-b-a) to 3-ethynylanyline of formula (IV-a):

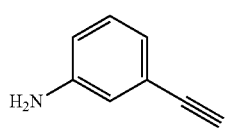

(k) Reaction of the 3-ethynylanyline of formula (IV-a) with 4-chloro-6,7-bis(2-methoxyethoxy)quinazoline of formula (III) to obtain Erlotinib of formula (I).
In both of these variants the substituent X1 is selected in the group consisting in nitro and NH(C=O)R where R is selected in the group $C_1$-$C_4$ alkyl i.e. among methyl, ethyl, n-propyl, isopropyl, n-butyl, isobutyl, sec-butyl and tert-butyl or it is an OR2 group in which R2 is selected in the $C_1$-$C_4$ alkyl group i.e. from among methyl, ethyl, n-propyl, isopropyl, n-butyl, isobutyl, sec-butyl and tert-butyl or it is a benzyl group. Preferably the reaction is conducted starting from the compound of formula (V-b) in which X1 is nitro or NHAc. Preferably the other substituent X is bromine.

The reaction conditions and the relative preferred aspects for conducting the step (f) according to the variant of the method described above are the same applied to the method as described in step (a).

The procedures, conditions and solvents used to perform the steps (b), (c), (d), (g), (h), (i) and (j) are known to an average man skilled in the art and widely addressed in the known art, part of which is indicated in the preceding section entitled State of the Art or in the Drug of the Future 2002, 27(10), 923-934 publication. The procedures indicated in the mentioned examples of the prior art are sufficiently described to allow obtaining the Erlotinib hydrochloride product.

EXPERIMENTAL PART

Example 1

Synthesis of 4-(3-aminophenyl)-2-methyl-3-butyn-2-ol of formula (IV)-exemplifying the invention

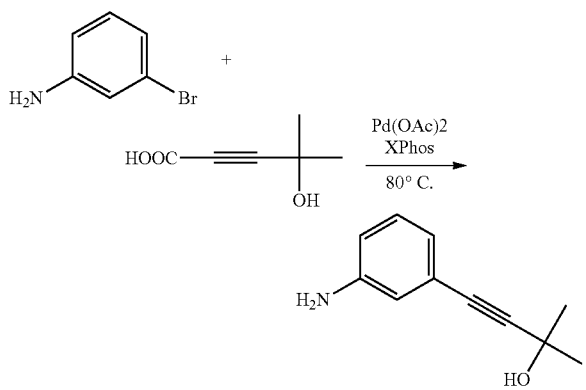

In a 3-liter 4-neck flask provided with a mechanical stirrer there are introduced—in the order—64.0 g (0.50 mol, 1.0 eq.) of 4-hydroxy-4-methyl-2-pentinoic acid, 5.7 g of Pd(OAc)$_2$ (5% mol), 24 g of XPhos (2-Dicyclohexylphosphino-2',4',6'-triisopropylbiphenyl; 10% mol) and 378 g (1.5 mol, 3 eq. mol.) of TBAF (Tetra-n-butylammonium fluoride). The mixture is dissolved, under Argon atmosphere, in 2 L of distilled anhydrous THF. 55 ml of 3-Bromoaniline (d=1.585 g/mL, 0.5 mol, 1.0 eq. mol.) are added to this solution.

The reaction is conducted under inert atmosphere for 14-16 hours at 80° C.

At the end of the reaction, the solvent is removed by distillation to residue at low pressure.

The residue is recovered using ethyl acetate (1500 ml) and water (1000 ml). The phases are separated and the aqueous phase is extracted 3 times using ethyl acetate (500 ml×3). The combined organic phases are dried on anhydrous Na₂SO₄ thus concentrated to dryness. Thus, 550 mL of isopropanol are added to the obtained solid and it is heated up to reflux for 15-30 minutes. The solution is hot filtered on a dicalite panel washing the panel using 80 mL of hot isopropanol, thus the filtrate is concentrated to dryness. The residue is re-crystalised from a mixture of 315 mL of toluene and 40 mL of isopropanol. The suspension is cooled to 0°-5° C. for 3 hours then filtered and the solid is washed using the same mixture of pre-cooled solvents. The product is dried at 45° C. 70.0 g are obtained for a molar yield equivalent to 80%.

Example 2

Example 1 is repeated under the same conditions except that 15.4 g of SPhos (2-Dicyclohexylphosphino-2',6'-dimethoxybiphenyl; 10% mol.) are used instead of XPhos (10% mol.).

73.6 g are obtained for a molar yield equivalent to 84%.

Example 3

Example 2 is repeated under the same conditions except that N-(3-bromophenyl)acetamide (compound of formula (V-b) where X=Br and X1=NHAc) is used instead of the 3-Bromoaniline substrate. The reaction is conducted at 90° C. instead of 80° C.

86.9 g of N-[3-(3-hydroxy-3-methylbut-1-yn-1-yl)phenyl] acetamide (compound of formula (IV-b) in which X1=NHAc) are obtained for a molar yield equivalent to 80%.

Example 4

Example 3 is repeated under the same conditions except that 2% millimolar of (PdAllylCl)₂ is used instead of Pd(OAc)₂. The reaction is always conducted at 90° C. The same product of example 3 is obtained with 84% molar yield.

Example 5

Example 2 is repeated under the same conditions except that 3-Chloroaniline is used instead of the 3-Bromoaniline substrate. The reaction after 24 hours is at 10% conversion and after 48 ore it is at 20% conversion to 4-(3-aminophenyl)-2-methyl-3-butyn-2-ol of formula (IV).

Example 6

Example 1 is repeated under the same conditions except that 1-Bromo-3-nitrobenzene (compound of formula (V-b) in which X=Br and X1=NO₂) are used instead of the 3-Bromoaniline substrate and using 2.0 eq. Mol. of 4-hydroxy-4-methyl-2-pentinoic acid instead of 1.0. The reaction leads to 2-methyl-4-(3-nitrophenyl)but-3-yn-2-ol (compound of formula (IV-b) in which X1=NO₂) with 840 molar yield.

Scrutinising the examples indicated above, it can be observed that the use of the conditions subject of the present invention allow obtaining the 4-(3-aminophenyl)-2-methyl-3-butyn-2-ol intermediate of formula (IV) or of formula (IV-b) and thus Erlotinib with good yields and avoiding the use of toxic catalysts.

Example 7

Synthesis of 3-Ethynylanyline of Formula (IV-a)—Exemplifying the Invention

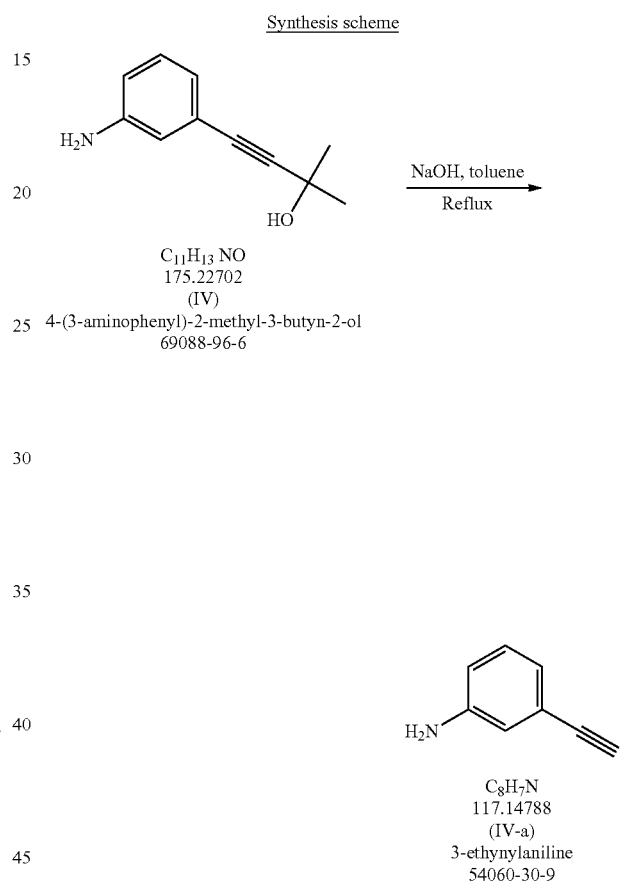

Synthesis scheme

C₁₁H₁₃ NO
175.22702
(IV)
4-(3-aminophenyl)-2-methyl-3-butyn-2-ol
69088-96-6

C₈H₇N
117.14788
(IV-a)
3-ethynylaniline
54060-30-9

Literature reference: US 2006/0188498

In a 500 ml flask provided with a thermometer, Dean-Stark apparatus and a drip funnel there are introduced—in succession at 25° C. and under nitrogen atmosphere—30 g of 4-(3-aminophenyl)-2-methyl-3-butyn-2-ol of formula (IV), 2.2 g of caustic soda and 240 mL of Toluene. The mixture is heated to the reflux temperature (105-110° C.) for 4 hrs, collecting the distillate in the Dean-Stark apparatus. Fresh toluene is simultaneously added to the reaction mixture so as to maintain a minimum volume of 180 ml (6 vol) within the flask. This allows removing acetone from the reaction mixture. After the 4 hours, it is stirred at reflux until the reaction is completed, controlling the trend thereof by means of TLC.

Upon completion of the reaction it is cooled to 25° C. and a mixture made up of 20 mL of Toluene and 250 mg of dicalite is added. The reaction mixture is stirred for 15 min. The reaction mixture is filtered and the solid is washed using 15 mL of Toluene. The filtrates are combined and the resulting solution is concentrated at 40° C. under vacuum up to residue. The product is obtained as oil (20.7 g) with quantitative yield.

Example 8

Synthesis of Erlotinib Hydrochloride of Formula (I)—Exemplifying the Invention

Synthesis scheme

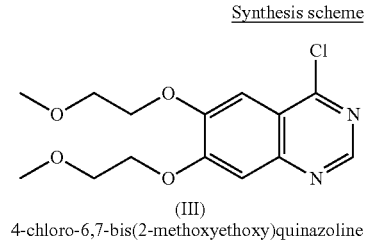

(III)
4-chloro-6,7-bis(2-methoxyethoxy)quinazoline

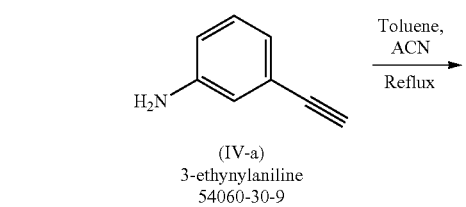

(IV-a)
3-ethynylaniline
54060-30-9

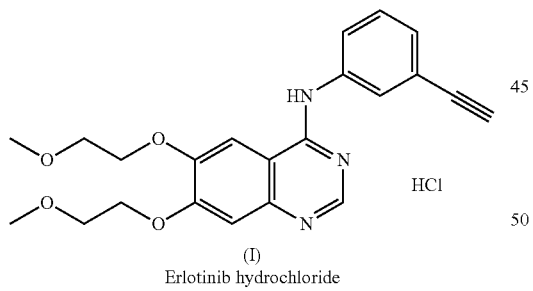

(I)
Erlotinib hydrochloride

Literature reference: US 2006/0188498.

In a 250 ml flask provided with a thermometer there are introduced—in succession at 25° C. and under nitrogen atmosphere—10 g of 4-chloro-6,7-bis(2-methoxyethoxy) quinazoline of formula (III), 80 mL of acetonitrile and a solution made up of 3.75 g of 3-ethynylanyline of formula (IV-a) (1 mol. equiv.) and 50 mL of toluene. The mixture is heated at the reflux temperature and controlled by means of TLC. Upon completing the reaction it is cooled to 25° C. and it is stirred for 2 hours. The reaction mixture is filtered and the solid is washed using 5 ml of acetonitrile. The product is dried under vacuum at 40° C. 12.1 g corresponding to an 88.0% molar yield are obtained. 4-chloro-6,7-bis(2-methoxyethoxy)quinazoline of formula (III) is a substance available in the market.

Example 9

Synthesis of 3-Butyn-2-ol, 4-[3-[[6,7-bis(2-methoxyethoxy)-4-quinazolinyl]amine]phenyl]-2-methyl-, hydrochloride (1:1) Of Formula (II)—Exemplifying the Invention Synthesis scheme

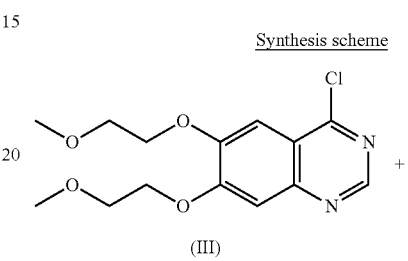

(III)

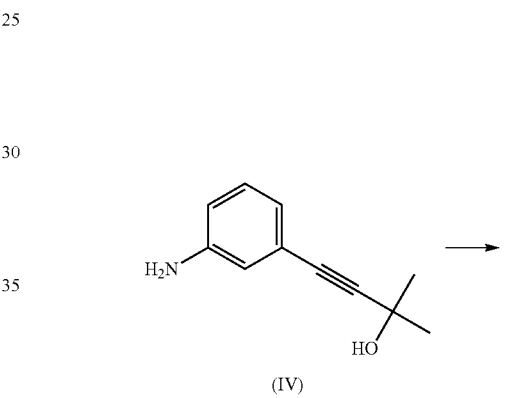

(IV)

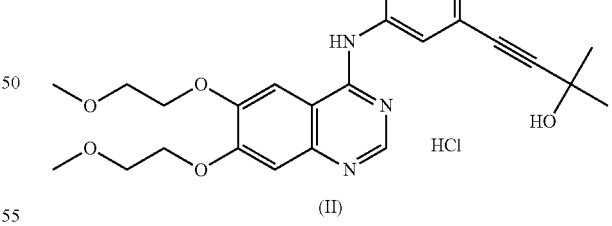

(II)

In a 500 ml flask provided with a thermometer there are introduced—in succession at 25° C. and under nitrogen atmosphere—15 g of 4-chloro-6,7-bis(2-methoxyethoxy) quinazoline of formula (III), 9.2 g of 4-(3-aminophenyl)-2-methyl-3-butyn-2-ol of formula (IV) and 225 mL of Acetonitrile. The mixture is heated at reflux for 5 hours. Upon completing the reaction the mixture is cooled to 0-5° C. and maintained at that temperature under stirring for at least 1 hour. The suspension is filtered and the solid is washed using 15 mL of cold Acetonitrile. The product is dried under vacuum for at least 8 hours obtaining 23.4 g of product as a white solid for a molar yield equivalent to 100%.

Example 10

Synthesis of Erlotinib Hydrochloride of Formula (I)—Exemplifying the Invention Synthesis scheme

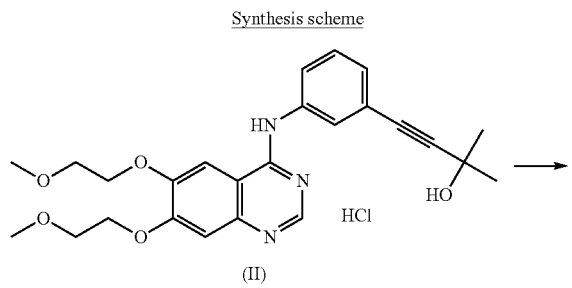

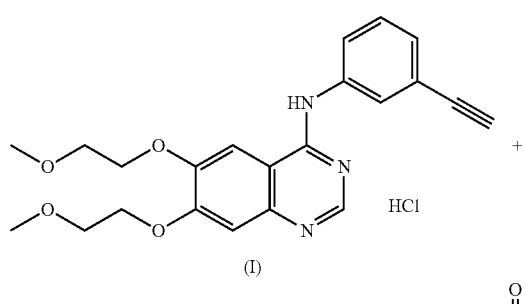

In a 500 ml flask provided with a thermometer there are introduced—in succession at 25° C. and under nitrogen atmosphere—32.3 g of 3-Butyn-2-ol, 4-[3-[[6,7-bis(2-methoxy-ethoxy)-4-quinazolinyl]amine]phenyl]-2-methyl-, hydrochloride (1:1) of formula (II), 300 mL of purified water and 600 mL of n-butanol. It is stirred at ambient temperature for 30 minutes. 50% aqueous NaOH is added up to a 10-12 pH. A limpid two-phase system is obtained. The phases are separated and the organic phase is concentrated at atmospheric pressure (thus azeotropically removing water) up to a residual volume of 300 mL. Thus 0.13 g of anhydrous solid NaOH are added and the resulting mixture is heated at reflux to 115-120° C. for 24 hours. Thus 150 mL of n-butanol are removed and the concentrated mixture is cooled to 15-25° C. A solution of 6.1 mL of concentrated HCl and 60 mL of n-butanol are thus dripped maintaining the temperature below 25° C. The obtained suspension is left under stirring over the whole night at 20-25° C. The suspension is filtered and the solid is washed using 25 mL of n-butanol. The solid is dried under vacuum at 45-50° C. 21 g of Erlotinib hydrochloride are obtained for a molar yield equivalent to 740.

Example 11

Synthesis of 4-(3-aminophenyl)-2-methyl-3-butyn-2-ol of Formula (IV) hydrochloride—Exemplifying the Invention Synthesis scheme

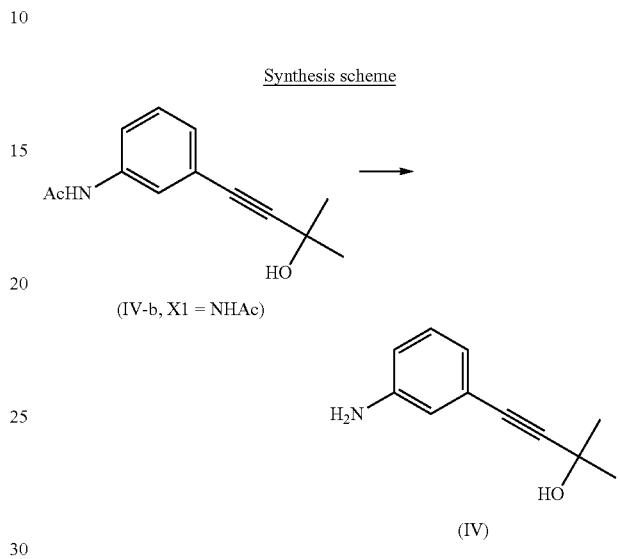

In a 100 ml flask provided with a thermometer there are introduced—in succession at 25° C. and under nitrogen atmosphere—2.0 g of N-[3-(3-hydroxy-3-methylbut-1-yn-1-yl) phenyl]acetamide of formula (IV-b, X1=NHAc) and 50 mL of HCl 1.2N. It is brought to reflux for 9 hours. Upon completing the reaction it is cooled to 40° C. and it is dried under vacuum to residue. 1.95 g of product are obtained as hydrochloride salt for a molar yield equivalent to 1000.

Example 12

Synthesis of 4-(3-aminophenyl)-2-methyl-3-butyn-2-ol of Formula (IV)—Exemplifying the Invention Synthesis scheme

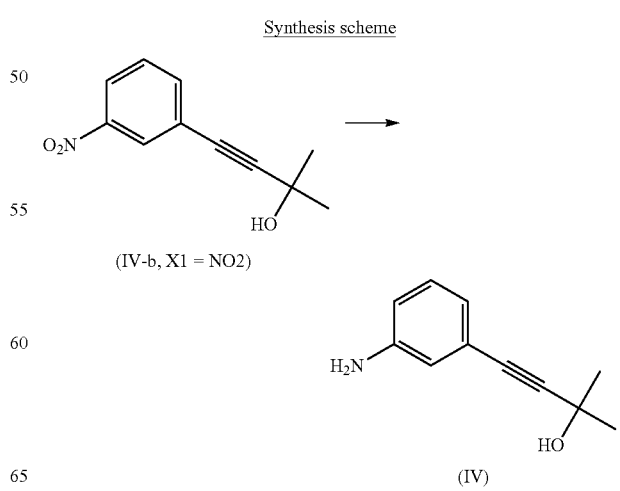

In an autoclave there are introduced—under nitrogen atmosphere—20.0 g of 2-methyl-4-(3-nitrophenyl)but-3-yn-2-ol and 300 mL of Isopropanol and 1.0 g of cobalt polysulfide paste (see U.S. Pat. No. 4,219,679A1). The mixture was hydrogenated for 1 hr and 15 minutes at 110° C. and 1000 psig of hydrogen pressure. After removing the catalyst by filtering, the solution was concentrated to dryness and the residue was crystallised from Toluene providing 13.1 g of the product of formula (IV) for a molar yield of 77%.

What we claim is:

1. A method for the preparation of Erlotinib of formula (I) or a salt thereof:

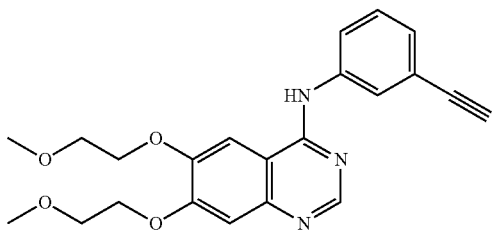
(I)

comprising the following steps:
(a) Reaction of the 3-substituted aniline of formula (V-a):

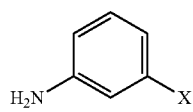
(V-a)

where X is selected from the group consisting in Iodine, Bromine, Chlorine, OTs, OMs, with 4-hydroxy-4-methyl-2-pentinoic acid of formula (V):

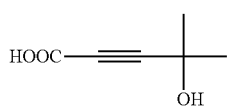
(V)

to obtain 4-(3-aminophenyl)-2-methyl-3-butyn-2-ol of formula (IV):

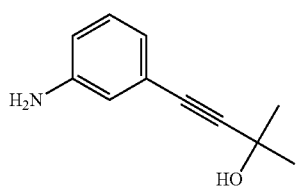
(IV)

(b) Reaction of the intermediate (IV) with 4-chloro-6,7-bis (2-methoxyethoxy)quinazoline of formula (III) to obtain 3-Butyn-2-ol, 4-[3-[[6,7-bis(2-methoxyethoxy)-4-quinazolinyl]amine]phenyl]-2-methyl-, hydrochloride (1:1) of formula (II):

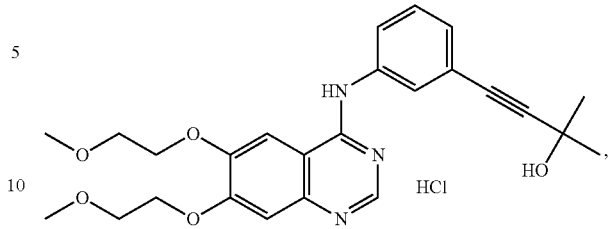
(II)

(c) Conversion of the intermediate (II) to Erlotinib of formula (I);

or a method wherein said steps (b) and (c) are replaced by the following steps:
(d) conversion of the intermediate (IV) to 3-ethynylanyline of formula (IV-a):

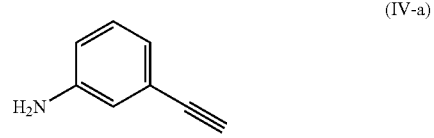
(IV-a)

(e) Reaction of the intermediate of formula (IV-a) with 4-chloro-6,7-bis(2-methoxyethoxy)quinazoline of formula (III) to obtain Erlotinib of formula (I).

2. A method according to claim 1, comprising the further step of converting the Erlotinib of formula (I) into Erlotinib hydrochloride.

3. A method according to claim 1, wherein the 3-substituted aniline is 3-Bromoaniline.

4. A method according to claim 1, wherein step (a) is conducted in presence of a catalytic system constituted by Pd (II) and a phosphine ligand.

5. A method according to claim 4, wherein the phosphine ligand is selected from among 2-dicyclohexylphosphino-2', 4',6'-triisopropylbiphenyl and 2-dicyclohexylphosphino-2', 6'-dimethoxybiphenyl.

6. A method according to claim 4, wherein palladium is used at molar amounts ranging from about 1% to about 10% molar with respect to 3-substituted aniline.

7. A method according to claim 1, wherein step (a) is conducted in THF.

8. A method according to claim 1, wherein 4-hydroxy-4-methyl-2-pentinoic acid of formula (V) is prepared by reacting acetone with propargylic acid.

9. A method according to claim 8, wherein said reaction is conducted in acetone.

10. A method according to claim 8, wherein said reaction is conducted in presence of a base.

11. A method for the preparation of 4-(3-aminophenyl)-2-methyl-3-butyn-2-ol of formula (IV):

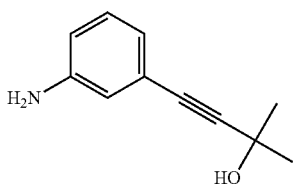
(IV)

or a salt thereof, comprising the reaction of the 3-substituted aniline of formula (V-a):

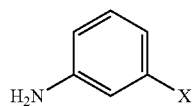
(V-a)

where X is selected from the group consisting in Iodine, Bromine, Chlorine, OTs, OMs, with 4-hydroxy-4-methyl-2-pentinoic acid of formula (V):

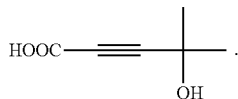
(V)

12. A method according to claim 11 comprising the further conversion of 4-(3-aminophenyl)-2-methyl-3-butyn-2-ol of formula (IV) into Erlotinib of formula (I).

13. A method according to claim 11, wherein the 3-substituted aniline is 3-Bromoaniline or the compound of formula (V-b) is N-(3-bromophenyl)acetamide or 1-Bromo-3-nitrobenzene.

14. A method according to claim 11, wherein the reaction is conducted in the presence of a catalytic system constituted by Pd (II) and a phosphine ligand.

15. A method according to claim 11, wherein 4-(3-aminophenyl)-2-methyl-3-butyn-2-ol of formula (IV) is converted into 3-ethynylanyline of formula (IV-a):

(IV-a)

16. A method according to claim 6, wherein the palladium is used at molar amounts of about 5% with respect to the 3-substituted aniline.

* * * * *